United States Patent
Dell'Orco et al.

(10) Patent No.: US 7,259,251 B1
(45) Date of Patent: *Aug. 21, 2007

(54) 3' UTR OF THE HUMAN PROHIBITIN GENE

(75) Inventors: Robert T. Dell'Orco, Derwood, MD (US); Eldon R. Jupe, Norman, OK (US); J. Keith McClung, Radford, VA (US); Xiao-Tie Liu, Chicago, IL (US); Robert L. King, Eagle Pass, TX (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/973,689

(22) PCT Filed: Jun. 7, 1996

(86) PCT No.: PCT/US96/09687

§ 371 (c)(1),
(2), (4) Date: Feb. 26, 1998

(87) PCT Pub. No.: WO96/40919

PCT Pub. Date: Dec. 19, 1996

Related U.S. Application Data

(63) Continuation-in-part of application No. 08/473,486, filed on Jun. 7, 1995, now Pat. No. 5,922,852.

(51) Int. Cl.
*C07H 21/02* (2006.01)
*C07H 21/04* (2006.01)
(52) U.S. Cl. .................................... 536/23.1; 536/24.3
(58) Field of Classification Search ............... 536/23.1, 536/23.5, 24.1, 24.3; 435/6
See application file for complete search history.

(56) References Cited

U.S. PATENT DOCUMENTS

| | | | |
|---|---|---|---|
| 5,401,635 A | | 3/1995 | Nakamura et al. ............. 435/6 |
| 5,776,738 A | * | 7/1998 | Dell Orco .................. 435/91.2 |
| 5,922,852 A | * | 7/1999 | Dell'Orco et al. ....... 435/320.1 |

FOREIGN PATENT DOCUMENTS

WO    WO96/40919    * 12/1996

OTHER PUBLICATIONS

Sequence alignment between Seq ID No. 3 and Seq ID No. 10.*
Asamoto, M. and Cohen, S.M., "Prohibitin gene is overexpressed but not mutated in rat bladder carcinomas and cell lines" *Cancer Let* 83:201-207 (1994).
Black, D. and Solomon, E., "The search for the familial breast/ovarian cancer gene," *Trends in Genetics* 9:22-26 (1993).
Black, et al., "A somatic cell hybrid map of the long arm of human chromosome 17, containing the familial breast cancer locus (BRCAl)," *Am J Hum Genet* 52:702-710 (1993).
Castilla, et al., "Mutations in the *BRCA1* gene in families with early-onset breast and ovarian cancer," *Nature Genetics* 8:387-391 (1993).
Choongkittaworn, et al., "Expression of prohibitin in rat seminiferous epithelium," *Biology of Reproduction* 49:300-310 (1993).
Cliby, et al., "Absence of prohibitin gene mutations in human epithelial ovarian tumors," *Gynecologic Oncology* 50:34-37 (1993).
Davis, S. and Watson, J.S., "In vitro activation of the interferon-induced, double-stranded RNA-dependent protein kinase PKR by RNA from the 3' untranslated regions of human α-tropomyosin," *Proc Natl Acad Sci USA* 93:508-513 (1996).
Deisseroth, et al., "Genetic therapy of human neoplastic disease," *Proc Am Assoc Cancer Res* 36:655-656 (1995).
Gross-Bellard, et al., "Isolation of high-molecular-weight DNA from mammalian cells," *Eur J Biochem* 36:32-38 (1973).
Holmes D.S. and Quigley, M., "A rapid boiling method for the preparation of bacterial plasmids," *Anal Biochem* 114:193-197 (1981).
Hongyo, et al., "'Cold SSCP': a simple, rapid and nonradioactive method for optimized single-strand conformation polymorphism analyses," *Nuc Acids Res* 21:3637-3642 (1993).
*Internal Medicine*, 4th edition; editor-in-chief Jay Stein, pp. 699-715.
Jupe, et al., "Lack of heterozygosity for prohibitin in breast cancer cell lines," *Proc Am Assoc Cancer Res* 36:569 (abstract 3390) (1995).
Jupe, et al., "Prohibitin antiproliferative activity and lack of heterozygosity in immortalized cell lines," *Exp Cell Res* 218:577-580 (1995).
Jupe, et al., "The loss of prohibitin's tumor suppressor activity in breast cancer is associated with mutations in its 3' untranslated region," *48th Annual Symposium on Fundamental Cancer Research. Genetic Mechanisms of Cancer*, Abstract C-62, Oct. 17-20, 1995.
Jupe, et al., "Prohibitin and breast cancer susceptibility," *35th Annual Meeting of The American Society for Cell Biology*, Abstract 2008, p. 346a, Dec. 13, 1995.
Jupe, et al., "The 3' untranslated region of prohibitin and cellular immortalization," *Experimental Cell Res* 224:128-135 (1996).
Jupe, et al., "Mutations in the 3' untranslated region (3' UTR) of prohibitin are related to loss of function and are diagnostic for breast cancer," *Proc Am Assoc Cancer Res* 37:583, Abstract 4000 (1996).
Jupe, et al., "Prohibitin in breast cancer cell lines: loss of antiproliferative activity is linked to 3' untranslated region mutation," *Cell Growth & Differentiation* 7:871-878 (1996).
Liu, et al., "Prohibitin expression during cellular senescence of human diploid fibroblasts," *Biochem Biophys Res Comm* 201:409-414 (1994).
Manjeshwar, et al., "Prohibitin as a diagnostic for breast cancer susceptibility and tumor development in stained slides of tissue section," *Proc Am Assoc Cancer Res* 37:257, Abstract 1751 (1996).
McClung, et al., "Isolation of a cDNA hybrid selects antiproliferative mRNA from rat liver," *Biochem Biophys Res Comm* 164:1316-1322 (1989).

(Continued)

*Primary Examiner*—Teresa E. Strzelecka
(74) *Attorney, Agent, or Firm*—Fulbright & Jaworski, LLP

(57) ABSTRACT

The 3' untranslated region of the human prohibitin gene has been isolated for use in a cancer susceptibility screen and as a therapeutic agent for the treatment of cancer.

11 Claims, 2 Drawing Sheets

OTHER PUBLICATIONS

Nuell, et al., "Prohibitin, an evolutionarily conserved intracellular protein that blocks DNA synthesis in normal fibroblasts and HeLa cells," *Mol Cell Biol* 11:1372-1381 (1991).

Orkin, et al., "Report and recommendation of the panel to assess the NIH investment in research on gene therapy," issued by National Institutes of Health (1995).

Sato, et al., "The human prohibitin gene located on chromosome 17q21 is mutated in sporadic breast cancer," *Cancer Res* 52:1643-1646 (1992).

Suggs, et al., "Use of synthetic oligonucleotides as hybridization probes: isolation of cloned cDNA sequences for human $\beta_2$-microglobulin," *Proc Natl Acad Sci* 78:6613-6617 (1981).

Terashima, et al., "The IgM antigen receptor of B lymphocytes is associated with prohibitin and a prohibitin-related protein," *EMBO J* 13:3782-3892 (1994).

Tokino, et al., "Absence of germline prohibitin mutations in early onset breast cancer," *International J Oncology* 3:769-772 (1993).

White, et al., "Assignment of the human prohibitin gene (PHB) to chromosome 17 and identification of a DNA polymorphism," *Genomics* 11:228-230 (1991).

Rastinejad, et al., "Tumor suppression by RNA from the 3' untranslated region of $\alpha$-tropomyosin," *Cell* 75:1107-1117 (1993).

Saiki, et al., "Enzymatic amplification of $\beta$-globin genomic sequences and restriction site analysis for diagnosis of sickle cell anemia," *Science* 230:1350-1354 (1985).

Sato, et al., "The human prohibitin (PHB) gene family and its somatic mutations in human tumors," *Genomics* 17:762-764 (1993).

\* cited by examiner

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
        (A) LENGTH: 230 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:1:

```
CCGTCCATCA CAACTGAGAT CCTCAAGTCA GTGGTGGTGA GTGAACAGGG GCCTTTAGCT      60

CGAGCCCAGA GCACCACCCT GGGAGGGCCC CAGGTGGCAG GAAGCGCTTG GCAGTGGGTT     120

GGTTGGGATG TGGCTGCTAG TTTCCTGGTT CCTTTTCTGC TTCCTCATTA ACCTGACCTG     180

CCCTTCTGCT CCTCCCTTTG AAACCAGGCT CGCTTTGATG CTGGAGAACT                230
```

(2) INFORMATION FOR SEQ ID NO:2:

(i) SEQUENCE CHARACTERISTICS:
        (A) LENGTH: 852 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens (xi) SEQUENCE DESCRIPTION: SEQ ID NO:2:

```
CCCAGAAATC ACTGTGAAAT TCATGATTG GCTTAAAGTG AAGGAAATAA AGGTAAAATC       60

ACTTCAGATC TCTAATTAGT CTATCAAATG AAACTCTTTC ATTCTTCTCA CATCCATCTA     120

CTTTTTTATC CACCTCCCTA CCAAAAATTG CCAAGTGCCT ATGCAAACCA GCTTTAGGTC     180

CCAATTCGGG GCCTGCTGGA GTTCCGGCCT GGGCACCAGC ATTTGGCAGC ACGCAGGCGG     240

GGCAGTATGT GATGGACTGG GGAGCACAGG TGTCTGCCTA GATCCACGTG TGGCCTCCGT     300

CCTGTCACTG ATGGAAGGTT TGCGGATGAG GGCATGTGCG GCTGAACTGA GAGGACAGGC     360

CTCCGTCTTC CCAGCGGTTC CTGCGCAGAT GCTGCTGAAG AGAGGTGCCG GGGAGGGGCA     420

GAGAGGAAGT GGTCTGTCTG TTACCATAAG TCTGATTCTC TTTAACTGTG TGACCAGCGG     480

AAACAGGTGT GTGTGAACTG GGCACAGATT GAAGAATCTG CCCCTGTTGA GGTGGGTGGG     540

CCTGACTGTT GCCCCCCAGG GTCCTAAAAC TTGGATGGAC TTGTATAGTG AGAGAGGAGG     600

CTTGGACCGA GATGTGAGTC CTGTTGAAGA CTTCCTCTCT ACCCCCCACC TTGGTCCCTC     660

TCAGATACCC AGTGGAATTC CAACTTGAAG GATTGCATCC TGCTGGGGCT GAACATGCCT     720

GCCAAAGACG TGTCCGACCT ACGTTCCTGG CCCCCTCGTT CAGAGACTGC CCTTCTCACG     780

GGCTCTATGC CTGCACTGGG AAGGAAACAA ATGTGTATAA ACTGCTGTCA ATAAATGACA     840

CCCAGACCTT CC                                                         852
```

(2) INFORMATION FOR SEQ ID NO:3:

(i) SEQUENCE CHARACTERISTICS:
        (A) LENGTH: 852 base pairs

```
            (B) TYPE: nucleic acid
            (C) STRANDEDNESS: double
            (D) TOPOLOGY: linear (ii) MOLECULE TYPE: DNA (genomic)

(vi) ORIGINAL SOURCE:
            (A) ORGANISM: Homo sapiens (xi) SEQUENCE DESCRIPTION: SEQ ID NO:3:

CCCAGAAATC ACTGTGAAAT TCATGATTG GCTTAAAGTG AAGGAAATAA AGGTAAAATC      60

ACTTCAGATC TCTAATTAGT CTATCAAATG AAACTCTTTC ATTCTTCTCA CATCCATCTA     120

CTTTTTTATC CACCTCCCTA CCAAAAATTG CCAAGTGCCT ATGCAAACCA GCTTTAGGTC     180

CCAATTCGGG GCCTGCTGGA GTTCCGGCCT GGGCACCAGC ATTTGGCAGC ACGCAGGCGG     240

GGCAGTATGT GATGGACTGG GGAGCACAGG TGTCTGCCTA GATCCACGTG TGGCCTCCGT     300

CCTGTCACTG ATGGAAGGTT TGCGGATGAG GGCATGTGCG GCTGAACTGA GAAGGCAGGC     360

CTCCGTCTTC CCAGCGGTTC CTGTGCAGAT GCTGCTGAAG AGAGGTGCCG GGGAGGGGCA     420

GAGAGGAAGT GGTCTGTCTG TTACCATAAG TCTGATTCTC TTTAACTGTG TGACCAGCGG     480

AAACAGGTGT GTGTGAACTG GGCACAGATT GAAGAATCTG CCCCTGTTGA GGTGGGTGGG     540

CCTGACTGTT GCCCCCCAGG GTCCTAAAAC TTGGATGGAC TTGTATAGTG AGAGAGGAGG     600

CCTGGACCGA GATGTGAGTC CTGTTGAAGA CTTCCTCTCT ACCCCCCACC TTGGTCCCTC     660

TCAGATACCC AGTGGAATTC CAACTTGAAG GATTGCATCC TGCTGGGGCT GAACATGCCT     720

GCCAAAGACG TGTCCGACCT ACGTTCCTGG CCCCCTCGTT CAGAGACTGC CCTTCTCACG     780

GGCTCTATGC CTGCACTGGG AAGGAAACAA ATGTGTATAA ACTGCTGTCA ATAAATGACA     840

CCCAGACCTT CC                                                        852

(2) INFORMATION FOR SEQ ID NO:4:

(i) SEQUENCE CHARACTERISTICS:
            (A) LENGTH: 852 base pairs
            (B) TYPE: nucleic acid
            (C) STRANDEDNESS: double
            (D) TOPOLOGY: linear (ii) MOLECULE TYPE: DNA (genomic)

(vi) ORIGINAL SOURCE:
            (A) ORGANISM: Homo sapiens (xi) SEQUENCE DESCRIPTION: SEQ ID NO:4:

CCCAGAAATC ACTGTGAAAT TCATGATTG GCTTAAAGTG AAGGAAATAA AGGTAAAATC      60

ACTTCAGATC TCTAATTAGT CTATCAAATG AAACTCTTTC ATTCTTCTCA CATCCATCTA     120

CTTTTTTATC CACCTCCCTA CCAAAAATTG CCAAGTGCCT ATGCAAACCA GCTTTAGGTC     180

CCAATTCGGG GCCTGCTGGA GTTCCGGCCT GGGCACCAGC ATTTGGCAGC ACGCAAGCGG     240

GGCAGTATGT GATGGACTGG GGAGCACAGG TGTCTGCCTA GATCCACGTG TGGCCTCCGT     300

CCTGTCACTG ATGGAAGGTT TGCGGATGAG GGCATGTGCG GCTGAACTGA GAAGGCAGGC     360

CTCCGTCTTC CCAGCGGTTC CTGTGCAGAT GCTGCTGAAG AGAGGTGCCG GGGAGGGGCA     420

GAGAGGAAGT GGTCTGTCTG TTACCATAAG TCTGATTCTC TTTAACTGTG TGACCAGCGG     480

AAACAGGTGT GTGTGAACTG GGCACAGATT GAAGAATCTG CCCCTGTTGA GGTGGGTGGG     540

CCTGACTGTT GCCCCCCAGG GTCCTAAAAC TTGGATGGAC TTGTATAGTG AGAGAGGAGG     600

CCTGGACCGA GATGTGAGTC CTGTTGAAGA CTTCCTCTCT ACCCCCCACC TTGGTCCCTC     660
```

```
TCAGATACCC AGTGGAATTC CAACTTGAAG GATTGCATCC TGCTGGGGCT GAACATGCCT      720

GCCAAAGATG TGTCCGACCT ACGTTCCTGG CCCCCTCGTT CAGAGACTGC CCTTCTCACG      780

GGCTCTATGC CTGCACTGGG AAGGAAACAA ATGTGTATAA ACTGCTGTCA ATAAATGACA      840

CCCAGACCTT CC                                                         852
```

(2) INFORMATION FOR SEQ ID NO:5:

(i) SEQUENCE CHARACTERISTICS:
        (A) LENGTH: 852 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens (xi) SEQUENCE DESCRIPTION: SEQ ID NO:5:

```
CCCAGAAATC ACTGTGAAAT TCATGATTG GCTTAAAGTG AAGGAAATAA AGGTAAAATC       60

ACTTCAGATC TCTAATTAGT CTATCAAATG AAACTCTTTC ATTCTTCTCA CATCCATCTA      120

CTTTTTTATC CACCTCCCTA CCAAAAATTG CCAAGTGCCT ATGCAAACCA GCTTTAGGTC      180

CCAATTCGGG GCCTGCTGGA GTTCCGGCCT GGGCACCAGC ATTTGGCAGC ACGCAGGCGG      240

GGCAGTATGT GATGGACTGG GGAGCACAGG TGTCTGCCTA GATCCACGTG TGGCCTCCGT      300

CCTGTCACTG ATGGAAGGTT TGCGGATGAG GGCATGTGCG GCTGAACTGA GAAGGCAGGC      360

CTCCGTCTTC CCAGCGGTTC CTGTGCAGAT GCTGCTGAAG AGAGGTGCCG GGGAGGGGCA      420

GAGAGGAAGT GGTCTGTCTG TTACCATAAG TCTGATTCTC TTTAACTGTG TGACCAGCGG      480

AAACAGGTGT GTGTGAACTG GCACAGATT GAAGAATCTG CCCCTGTTGA GGTGGGTGGG      540

CCTGACTGTT GCCCCCCAGG GTCCTAAAAC TTGGATGGAC TTGTATAGTG AGAGAGGAGG      600

CCTGGACCGA GATGTGAGTC CTGTTGAAGA CTTCCTCTCT ACCCCCCACC TTGGTCCCTC      660

TCAGATACCC AGTGGAATTC CAACTTGAAG GATTGCATCC TGCTGGGGCT GAACATGCCT      720

GCCAAAGACG TGTCCGACCT ACGTTCCTGG CCCCCTCATT CAGAGACTGC CCTTCTCACG      780

GGCTCTATGC CTGCACTGGG AAGGAAACAA ATGCGTATAA ACTGCTGTCA ATAAATGACA      840

CCCAGACCTT CC                                                         852
```

(2) INFORMATION FOR SEQ ID NO:6:

(i) SEQUENCE CHARACTERISTICS:
        (A) LENGTH: 852 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens (xi) SEQUENCE DESCRIPTION: SEQ ID NO:6:

```
CCCAGAAATC ACTGTGAAAT TCATGATTG GCTTAAAGTG AAGGAAATAA AGGTAAAATC       60

ACTTCAGATC TCTAATTAGT CTATCAAATG AAACTCTTTC ATTCTTCTCA CATCCATCTA      120

CTTTTTTATC CACCTCCCTA CCAAAAATTG CCAAGTGCCT ATGCAAACCA GCTTTAGGTC      180

CCAATTCGGG GCCTGCTGGA GTTCCGGCCT GGGCACCAGC ATTTGGCAGC ACGCAAGCGG      240

GGCAGTATGT GATGGACTGG GGAGCACAGG TGTCTGCCTA GATCCACGTG TGGCCTCCGT      300
```

```
CCTGTCACTG ATGGAAGGTT TGCGGATGAG GGCATGTGCG GCTGAACTGA GAAGGCAGGC      360

CTCCGTCTTC CCAGCGGTTC CTGTGCAGAT GCTGCTGAAG AGAGGTGCCG GGGAGGGGCA      420

GAGAGGAAGT GGTCTGTCTG TTACCATAAG TCTGATTCTC TTTAACTGTG TGACCAGCGG      480

AAACAGGTGT GTGTGAACTG GGCACAGATT GAAGAATCTG CCCCTGTTGA GGTGGGTGGG      540

CCTGACTGTT GCCCCCCAGG GTCCTAAAAC TTGGATGGAC TTGTATAGTG AGAGAGGAGG      600

CCTGGACCGA GATGTGAGTC CTGTTGAAGA CTTCCTCTCT ACCCCCCACC TTGGTCCCTC      660

TCAGATACCC AGTGGAATTC CAACTTGAAG GATTGCATCC TGCTGGGGCT GAACATGCCT      720

GCCAAAGATG TGTCCGACCT ACGTTCCTGG CCCCCTCGTT CAGAGACTGC CCTTCTCACG      780

GGCTCTATGC CTGCACTGGG AAGGAAACAA ATGTGTATAA ACTGCTGTCA ATAAATGACA      840

CCCAGACCTT CC                                                         852

(2) INFORMATION FOR SEQ ID NO:7:

(i) SEQUENCE CHARACTERISTICS:
        (A) LENGTH: 852 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens (xi) SEQUENCE DESCRIPTION: SEQ ID NO:7:

CCCAGAAATC ACTGTGAAAT TTCATGATTG GCTTAAAGTG AAGGAAATAA AGGTAAAATC       60

ACTTCAGATC TCTAATTAGT CTATCAAATG AAACTCTTTC ATTCTTCTCA CATCCATCTA      120

CTTTTTTATC CACCTCCCTA CCAAAAATTG CCAAGTGCCT ATGCAAACCA GCTTTAGGTC      180

CCAATTCGGG GCCTGCTGGA GTTCCGGCCT GGGCACCAGC ATTTGGCAGC ACGCAGGCGG      240

GGCAGTATGT GATGGACTGG GGAGCACAGG TGTCTGCCTA GATCCACGTG TGGCCTCCGT      300

CCTGTCACTG ATGGAAGGTT TGCGGATGAG GGCATGTGCG GCTGAACTGA GAAGGCAGGC      360

CTCCGTCTTC CCAGCGGTTC CTGTGCAGAT GCTGCTGAAG AGAGGTGCCG GGGAGGGGCA      420

GAGAGGAAGT GGTCTGTCTG TTACCATAAG TCTGATTCTC TTTAACTGTG TGACCAGCGG      480

AAACAGGTGT GTGTGAACTG GGCACAGATT GAAGAATCTG CCCCTGTTGA GGTGGGTGGG      540

CCTGACTGTT GCCCCCCAGG GTCCTAAAAC TTGGATGGAC TTGTATAGTG AGAGAGGAGG      600

CCTGGACCGA GATGTGAGTC CTGTTGAAGA CTTCCTCTCT ACCCCCCACC TTGGTCCCTC      660

TCAGATACCC AGTGGAATTC CAACTTGAAG GATTGCATCC TGCTGGGGCT GAACATGCCT      720

GCCAAAGACG TGTCCGACCT ACGTTCCTGG CCCCCTCGTT CAGAGACTGC CCTTCTCACG      780

GGCTCTATGC CTGCACTGGG AAGGAAACAA ATGTGTATAA ACTGCTGTCA ATAAATGACA      840

CCCAGACCTT CC                                                         852

(2) INFORMATION FOR SEQ ID NO:8:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
```

(A) ORGANISM: Homo sapiens (xi) SEQUENCE DESCRIPTION: SEQ ID NO:8:

CCCAGAAATC ACTGTG                                                           16

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Homo sapiens (xi) SEQUENCE DESCRIPTION: SEQ ID NO:9:

GGAAGGTCTG GGTGTCATTT                                                       20

(2) INFORMATION FOR SEQ ID NO:10:

(i) SEQUENCE CHARACTERISTICS:
        (A) LENGTH: 1001 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:10:

TGAGGGCCCA CCCTGCCTGC ACCTCCGCGG GCTGACTGGG CCACAGCCCC GATGATTCTT           60

AACACAGCCT TCCTTCTGCT CCCACCCCAG AAATCACTGT GAAATTTCAT GATTGGCTTA          120

AAGTGAAGGA AATAAAGGTA AAATCACTTC AGATCTCTAA TTAGTCTATC AAATGAAACT          180

CTTTCATTCT TCTCACATCC ATCTACTTTT TTATCCACCT CCCTACCAAA AATTGCCAAG          240

TGCCTATGCA AACCAGCTTT AGGTCCCAAT TCGGGGCCTG CTGGAGTTCC GGCCTGGGCA          300

CCAGCATTTG GCAGCACGCA GGCGGGGCAG TATGTGATGG ACTGGGGAGC ACAGGTGTCT          360

GCCTAGATCC ACGTGTGGCC TCCGTCCTGT CACTGATGGA AGGTTTGCGG ATGAGGGCAT          420

GTGCGGCTGA ACTGAGAAGG CAGGCCTCCG TCTTCCCAGC GGTTCCTGTG CAGATGCTGC          480

TGAAGAGAGG TGCCGGGGAG GGGCAGAGAG GAAGTGGTCT GTCTGTTACC ATAAGTCTGA          540

TTCTCTTTAA CTGTGTGACC AGCGGAAACA GGTGTGTGTG AACTGGGCAC AGATTGAAGA          600

ATCTGCCCCT GTTGAGGTGG GTGGGCCTGA CTGTTGCCCC CCAGGGTCCT AAAACTTGGA          660

TGGACTTGTA TAGTGAGAGA GGAGGCCTGG ACCGAGATGT GAGTCCTGTT GAAGACTTCC          720

TCTCTACCCC CCACCTTGGT CCCTCTCAGA TACCCAGTGG AATTCCAACT TGAAGGATTG          780

CATCCTGCTG GGGCTGAACA TGCCTGCCAA AGACGTGTCC GACCTACGTT CCTGGCCCCC          840

TCGTTCAGAG ACTGCCCTTC TCACGGGCTC TATGCCTGCA CTGGGAAGGA AACAAATGTG          900

TATAAACTGC TGTCAATAAA TGACACCCAG ACCTTCCGGA TCAAAAAAAA AAAAAAAAA           960

AAAAAAAAAA AAAAAAAAAA AAAAAAAAAA AAAAAGGAAT T                             1001

(2) INFORMATION FOR SEQ ID NO:11:

(i) SEQUENCE CHARACTERISTICS:
        (A) LENGTH: 18 base pairs

```
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Homo sapiens (xi) SEQUENCE DESCRIPTION: SEQ ID NO:11:

CAATCACACT GCCTCATC                                                         18

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Homo sapiens (xi) SEQUENCE DESCRIPTION: SEQ ID NO:12:

TGAGTGCCGG AGAAAGGG                                                         18

(2) INFORMATION FOR SEQ ID NO:13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Homo sapiens (xi) SEQUENCE DESCRIPTION: SEQ ID NO:13:

CCGCTTCTGT GAACTCC                                                          17

(2) INFORMATION FOR SEQ ID NO:14:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Homo sapiens (xi) SEQUENCE DESCRIPTION: SEQ ID NO:14:

TGGAGGGACA GTGGGT                                                           16

(2) INFORMATION FOR SEQ ID NO:15:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
```

-continued (A) ORGANISM: Homo sapiens (xi) SEQUENCE DESCRIPTION: SEQ ID NO:15:

TCTAACTAGC TGCAAA                                            16

(2) INFORMATION FOR SEQ ID NO:16:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(vi) ORIGINAL SOURCE:
          (A) ORGANISM: Homo sapiens (xi) SEQUENCE DESCRIPTION: SEQ ID NO:16:

AGAGGATTTT TATGACATGT C                                      21

(2) INFORMATION FOR SEQ ID NO:17:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(vi) ORIGINAL SOURCE:
          (A) ORGANISM: Homo sapiens (xi) SEQUENCE DESCRIPTION: SEQ ID NO:17:

GAGCACCTCT TCCACACTCC C                                      21

(2) INFORMATION FOR SEQ ID NO:18:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: DNA (genomic)

(vi) ORIGINAL SOURCE:
          (A) ORGANISM: Homo sapiens (xi) SEQUENCE DESCRIPTION: SEQ ID NO:18:

GTGCTCTGGG CTCGAGC                                           17

(2) INFORMATION FOR SEQ ID NO:19:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(vi) ORIGINAL SOURCE:
          (A) ORGANISM: Homo sapiens (xi) SEQUENCE DESCRIPTION: SEQ ID NO:19:

CTAAAGGCCC CTGTTCACTC A                                      21

-continued (2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Homo sapiens (xi) SEQUENCE DESCRIPTION: SEQ ID NO:20:

```
CCTCATTAAC CTGACCTGCC C                                         21
```

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Homo sapiens (xi) SEQUENCE DESCRIPTION: SEQ ID NO:21:

```
TAAACGAGAA CTGCAGCCCC T                                         21
```

(2) INFORMATION FOR SEQ ID NO:22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Homo sapiens (xi) SEQUENCE DESCRIPTION: SEQ ID NO:22:

```
GCCTTTGGTT GTAGCCTG                                             18
```

(2) INFORMATION FOR SEQ ID NO:23:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Homo sapiens (xi) SEQUENCE DESCRIPTION: SEQ ID NO:23:

```
CACAGTGATT TCTGGGG                                              17
```

3' UTR OF THE HUMAN PROHIBITIN GENE

CROSS-REFERENCE TO RELATED APPLICATIONS

This application is a continuation-in-part of U.S. Application Ser. No. 08/473,486 filed Jun. 7, 1995, which issued as U.S. Pat. No. 5,922,852 on Jul. 13, 1999.

TECHNICAL FIELD

The present invention relates to the 3' untranslated region of the human antiproliferative gene prohibitin. The present invention also relates to use of the 3' untranslated region as a screening tool for determining susceptibility to cancer and as a therapeutic agent.

BACKGROUND OF THE INVENTION

Tumor suppressor genes are a class of genes identified on the basis of an association between neoplasia and the loss of function in both copies of the gene. Of the 15 to 20 tumor suppressor genes identified to date, retinoblastoma, p53, and Wilms' tumor have been investigated to the greatest extent.

Prohibitin, an evolutionarily conserved gene that possesses antiproliferative activity, is postulated to be a tumor-suppressor gene whose expression, when lost, contributes to the immortalization of cells from one or more of the four complementation groups proposed by Pereira-Smith. Jupe et al., *Exp Cell Res* 218:577-580 (1995). Its sequence, however, is unrelated to that of any previously cloned tumor suppressor gene. Nuell et al., *Mol Cell Biol* 11:1372-1381 (1991).

Because of the intracellular, antiproliferative activity of its gene product and its tumor-suppression potential, the prohibitin gene has been widely studied. A rat prohibitin has been described by McClung et al. McClung et al., *Biochem Biophys Res Comm* 164:1316-1322 (1989). The first full length prohibitin cDNA was isolated on the basis of a higher expression of prohibitin mRNA in non-dividing rat liver cells than in regenerating rat liver cells. It was subsequently reported that prohibitin mRNA microinjected into a cell blocked DNA synthesis and that microinjection of an antisense oligonucleotide stimulated cells to divide. The full length sequence of the rat prohibitin cDNA was described by Nuell et al. Nuell et al., *Mol Cell Biol* 11:1372-1381 (1991).

The human prohibitin gene was localized to chromosome 17q21 using both mouse-human hybrid cell line mapping and in situ hybridization to human metaphase chromosomes. White et al., *Genomics* 11:228-230 (1991). This region is very near the location of the familial breast cancer (BRCA 1) locus, and prohibitin was initially considered a candidate gene (Black, D. and Solomon, E., *Trends in Genetics* 9:22-26 (1993)); however, more recent genetic and cytogenetic mapping studies have ruled out prohibitin as the BRCA 1 gene. Black, et al., *Am J Hum Genet* 52:702-710 (1993).

At the mRNA level, it has been reported that the human prohibitin gene is expressed as two transcripts of 1.2 kb and 1.9 kb in normal human cells. Liu, et al., *Biochem Biophys Res Comm* 201:409-414 (1994). The difference between the two transcripts is an approximately 750 nucleotide sequence 3' to the end of the 1.2 kb transcript. Despite these differences, both code for the identical protein. Analyses have shown that the 1.9 kb transcript is expressed to a greater extent during the G1/S and S phases of the cell cycle in human populations (Liu et al., *Biochem Biophys Res Comm* 201:409-414 (1994)) and that this transcript is overexpressed in immortalized cell populations derived from human tumors. Jupe et al., *Exp Cell Res* 218:577-580 (1995).

Specifically, prohibitin is apparently involved in the process of immortalization in a group of human cells that are classified in complementation Group B proposed by Olivia Pereira-Smith. Cells classified in this group exhibit a unique prohibitin genotype. Upon Southern analysis of EcoRI digested DNA using a probe to intron 4 of prohibitin, DNA from Group B cells exhibit only one band at 5 kb. Normal DNA analyzed in the same way exhibits one of three banding patterns: two bands, one at 5 and one at 7 kb; one band at 5 kb; or one band at 7 kb. White et al., *Genomics* 11:228-230 (1991); Tokino et al., *Internatl J Onco* 3:769-772 (1993); Jupe et al., *Exp Cell Res* 218:577-580 (1995). DNA from cells classified in the other groups (A, C, D) exhibit one of two banding patterns, either one 7 kb band, or one 7 kb and one 5 kb band with the 7 kb band yielding a stronger signal; however, no sample from these complementation groups exhibit only the 5 kb band. These results indicate that prohibitin exists as two alleles, one of which contains an additional EcoRI cut site and is characterized by a 5 kb band on Southern analysis. Since only immortalized cells classified as Group B are uniformly homozygous for the allele yielding the 5 kb band, this allele has been designated the B type allele and the other allele yielding the 7 kb band has been designated the non-B type allele. Thus, it appears that the loss of heterozygosity plays a role in cellular immortalization of Group B cells.

A human prohibitin cDNA, including 134 nucleotides immediately 3' to the stop codon of the coding sequence, has been reported. In addition, mutations occurring in exon 4 and exon 5 of this sequence were found in material derived from four of twenty-three sporadic human breast tumors. Sato et al., *Cancer Res* 52:1643-1646 (1992). A study of the four most highly conserved exons of the prohibitin gene (exons 4 through 7) from DNA purified from blood samples from seventy-six familial breast cancer patients found no alterations in the prohibitin coding region, but they did find two additional intronic polymorphisms, one in intron 4 and one in intron 5. However, there was no evidence that any of the patients carried a germline change of the conserved prohibitin gene region. It was concluded that mutations in the prohibitin gene were not associated with the early onset, familial form of the disease. Tokino et al., *Internatl J Oncol* 3:769-772 (1993).

In a more extensive study, an RNase protection assay was used to screen 120 primary breast tumors that showed a loss of heterozygosity for the long arm of chromosome 17 and/or were derived from patients younger than age thirty-five. This assay was also used to test for prohibitin alterations in a number of ovarian, liver, and lung tumors. One additional mutation in one of the breast tumors and no mutations in any of the other samples were found. The investigators concluded that somatic mutations in prohibitin may be associated with sporadic breast tumors, but may not be a factor in a large number of other tumors, including early onset breast cancer. Sato et al., *Genomics* 17:762-764 (1993). This conclusion was reinforced by two additional studies. Cliby et al. found no mutations in prohibitin exons 4 or 5 from twenty human ovarian tumors (Cliby et al., *Gynecologic Oncology* 50:34-37 (1993)), and Asamoto and Cohen were unable to find prohibitin mutations in cDNAs from a series of rat bladder tumors and tumor cell lines (Asamoto, M. and Cohen, S. M., *Cancer Let* 83:201-207 (1994)).

While these studies presented evidence which indicated a lack of any relationship between inherited breast cancer and prohibitin mutations, whether an association existed between prohibitin mutations and sporadic or late onset breast cancer remained an unanswered question. The reported studies into the relationship between prohibitin mutations and sporadic or late onset breast cancer, however, focused on the coding region of the gene and whether its mutation(s) corresponded with the development of cancerous tumors.

It has now been found that mutations in the 3' untranslated region (UTR) of the B type allele are diagnostic for increased susceptibility to cancer, particularly breast cancer. Thus, the presence (or absence) of these mutations can be used as a screening tool for the early detection and treatment of cancer. In another embodiment, reintroduction of a normal 3' UTR into early stage tumors can be employed as a therapeutic agent for treatment of cancer.

SUMMARY OF THE INVENTION

The invention relates to a purified, wild-type nucleic acid fragment comprising the 3' untranslated region or UTR of the human prohibitin gene and sub-fragments thereof.

In another embodiment, this invention relates to a purified, non wild-type nucleic acid fragment comprising the 3' untranslated region of the human prohibitin gene and sub-fragments thereof.

In still another embodiment, this invention relates to the use of the nucleic acid fragments described above in assays diagnostic for susceptibility to cancer and as therapeutic agents for the treatment of cancer.

DETAILED DESCRIPTION

Figure 1:
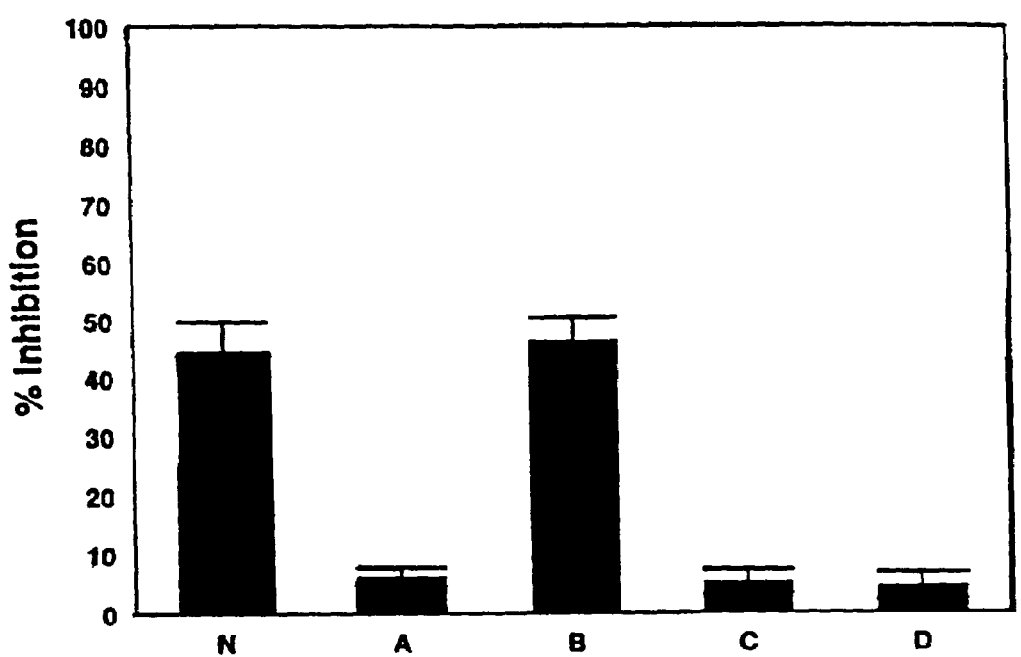
FIG. 1 is a bar graph showing the inhibition of cell cycle progression by microinjection of prohibitin transcripts into normal and immortalized cells. The bars show the mean±the standard error of means from at least three experiments. The samples are designated as follows: N,CF-3, normal HDF; A,EJ, bladder carcinoma; B,HeLa, cervical carcinoma; C,TE85, osteosarcoma; and D,A1698, bladder carcinoma.

The distribution of the prohibitin genotype in the general population and its distribution in tumors, preferably breast tumors, can be used to perform a two part screening by which the probability of an individual developing cancer can be predicted. These probabilities would range from those with a very low probability to those with an extremely high probability. Individuals who are heterozygous for the two prohibitin alleles would be predicted to have little risk for developing cancer. This probability would increase for those who are homozygous for the B type allele and who have a defect in the 3' UTR of at least one of the alleles. Therefore, the screening would be in two parts.

The first part would be a determination of the individual's prohibitin genotype using, e.g., one of the following techniques: polymerase chain reaction (PCR) amplification of a 191 bp region surrounding the intron 5/exon 6 junction and single strand conformation polymorphism (SSCP) analysis of the resulting fragment; PCR amplification of a 76 bp region surrounding the intron 5/exon 6 splice site and digestion of the resulting fragment with BsmAI endonuclease; and/or RFLP assays of genomic DNA on Southern blots if sufficient amounts of DNA are available. For those identified as being homozygous for the B type allele, a second screening for alterations in the 3' UTR would be conducted. For example, sequencing of the 3' UTR would identify specific base changes from the wild type sequence. Alternatively, if sequence analyses identify specific base changes in the majority of the samples, a RFLP analysis could be developed if these base changes resulted in the loss or the gain of a specific cut site. Additionally, SSCP analyses of various portions of the entire 3' UTR would be undertaken after PCR amplification of the regions.

Where screening is performed at a young age, increased surveillance will result in earlier detection, earlier treatment, and improved survivorship. Additionally, it is envisioned that the reintroduction of a normal 3' UTR into early stage tumors would be of therapeutic value.

To determine an individual's prohibitin genotype, genomic DNA can be isolated, e.g., from blood lymphocytes by standard techniques as described by Castilla et al. (Castilla et al., *Nature Genetics* 8:387-391 (1993)) incorporated herein by reference. Following the preparation of genomic DNA, preferably as described in Example 1, the region containing intron 5/exon 6 is amplified using PCR. Preferably, PCR is performed under the conditions set forth in Example 1. More preferably, either a 76 bp fragment or a 191 bp fragment encompassing intron 5/exon 6 is produced using the sense and antisense primers disclosed in Example 6.

Once the intron 5/exon 6 region has been amplified, the genotype is determined by using a restriction fragment length polymorphism (RFLP) analysis, and/or a single strand conformation polymorphism (SSCP) assay, preferably as described in Examples 8 and 9, respectively. Alternatively, the prohibitin genotype can be determined by Southern analysis of human genomic DNA digested with EcoRI and probed with a labeled fragment from intron 4. A Southern analysis identifies two distinct restriction fragment length polymorphisms in the human population. Individuals are homozygous for an allele that produces a 7 kb band (non-B type allele) or an allele that has an additional EcoRI site in an intron that produces a 5 kb and a 2 kb band (B type allele). Genomic DNA from human cells is isolated by standard methods such as those described in Example 1. The restriction digests are performed according to the manufacturer's instructions and analyzed using agarose gel electrophoresis. The intron 4 probe can be prepared by standard PCR amplification. Procedures are described in Example 1 using a sense primer consisting of the first 18 bases at the 5' end of a 230 bp segment of intron 4 (SEQ ID NO: 1) and an antisense primer consisting of the bases complementary to the last 18 bases at the 3' end of this 230 bp segment.

For those identified as homozygous for the B-type allele alterations in the 3' UTR can be determined by amplifying the 3' UTR by PCR and then assaying it using a SSCP and/or a RFLP assay, preferably a SSCP assay. PCR amplification of the 3' UTR is preferably performed under the conditions set forth in Example 1 using the sense and antisense primers set forth in Example 4, while the SSCP analysis of the 3'UTR is preferably performed as described in Example 13.

Alternatively, alterations in the 3' UTR can be ascertained by sequencing the 3' UTR region, preferably as described in Example 1.

Where an individual is identified as high risk on the basis of the above-identified test, a wild-type 3' UTR can be reintroduced into the tumors, preferably according to Example 11.

While the invention has been described in terms of the methods and materials described in the examples, it is to be understood that it is well within the skill of one within the art to modify these standard methods and materials to suit their particular needs.

EXAMPLES

The relationship between homozygosity for the B type allele, i.e., the 5 kb allele, and cells classified as belonging to complementation Group B was pursued using single strand conformational polymorphism (SSCP) analysis following PCR amplification of the coding region of the human prohibitin gene from several immortalized populations, including the following four cell lines classified as belonging to Group B: cervical carcinoma, transformed skin fibroblasts, glioblastoma, and bladder carcinoma (Table 1). Data indicate that the EcoRI RFLP marker is genetically linked to another marker initially detected as a single stranded conformation polymorphism (SSCP) in PCR products containing exon 6 and a portion of its flanking introns. (See Example 9) Sequencing showed that the coding region from these populations was identical to that of the coding region from normal human DNA obtained from normal cell lines and from purchased normal tissue samples (Tables 2, 3, 4 and 5).

A similar analysis of selected regions of the prohibitin gene from a limited number of breast cancer cell lines (Table 6) also indicated that the protein coding region of the prohibitin gene was apparently unaltered in these cells; however, all DNA samples classified as being from cells homozygous for the B type allele exhibited a band shift when the PCR amplification of exon 6 was analyzed. Cloning and DNA sequencing analysis of this region showed that this band shift is the result of a base difference in intron 5 (c/g) occurring 12 nucleotides 5' to the intron/exon junction with exon 6. In the B type allele, a BsmAI cleavage site is missing while in the non-B type allele the site is present. The B type allele is defined by two markers, the presence of the additional intron EcoRI site and the absence of the intron BsmAI site. In contrast, non-B type alleles lack the EcoRI site and have the BsmAI site.

Although both of these RFLP's had been previously recognized, neither their genetic linkage nor their relevance to cellular immortalization had been established. The significance of these prohibitin markers to breast cancer was examined (Jupe et al., *Proc Am Assoc Cancer Res* 36:569 (1995)) in a survey of 17 breast cancer cell lines using the EcoRI and BsmAI RFLP's described above. This survey identified 14 homozygous B type lines and 3 non-homozygous non-B type lines. None of the breast cancer cell lines had a heterozygous genotype.

In another study, seventeen of twenty-two breast cancer cell lines obtained from the American Type Culture Collection (ATCC) were found to be homozygous for the allele characteristic of cells belonging to complementation Group B. (See Table 7) None were found to be heterozygous for the two prohibitin alleles. In contrast, about 50% of normal individuals (200 syrveyed) are heterozygous for the two alleles. Only cells homozygous for the B type allele are sensitive to the antiproliferative activity of prohibitin. Jupe, E. R. et al., *Exp Cell Res* (In press)

Because of the relationship between the homozygosity of the B type allele in Group B cells, the 80% incidence of this genotype in breast cancer cell lines, and the increase in expression of the 1.9 kb transcript in immortalized cells, an analysis of the 3' UTR consisting of the entire nucleotide sequence 3' to the end of the sequence coding for the 1.2 kb transcript was undertaken. Initial sequencing data show that this region from HeLa cells (SEQ ID NO:2), which are classified as Group B, contains four base changes when compared to clones of the same region from the following: (1) a normal human fibroblast cell line, IMR-90, which is homozygous for the wild-type B type allele (SEQ ID NO:3); and (2) an immortalized cell line, CMV-Mj-HEL-1, classified in Group C and homozygous for the non-B type allele. The mutated nucleotides of the HeLa cells were at positions 353, 355, 384 and 602 (SEQ ID NO:2).

Nucleotide sequence information from three cell lines that were derived from breast tumors was also obtained. Each of these cell lines, BT-20, MCF-7, and SK-BR-3 are homozygous for the B type prohibitin allele and are, therefore, classified in complementation group B. Additionally, each exhibit 3' UTR sequences that are different from the wild-type prohibitin gene. Mutated bases were found at positions 236 and 729 in MCF-7 (SEQ ID NO:4) and at positions 758 and 814 in BT-20 (SEQ ID NO:5). In SK-BR-3 cells, 35 base changes were detected. (See Table 8)

The significance of these base changes is emphasized by results derived from clinical breast tumor samples. DNA from four breast tumors obtained from Dr. F. Schaefer from the Chapman Institute of Tulsa, Okla., and DNA isolated from breast tumors and matched normal tissue from four patients obtained from the Cooperative Human Tissue Network of the National Institutes of Health were analyzed for their prohibitin genotype [Chapman Sample Numbers: BC 102, BC 103, BC 104, BC 105; Cooperative Human Tissue Network Sample Numbers: 4001490-H (Tumor) and 4001490-Q (Normal), 4001536-AT (Tumor) and 4001536-AY (Normal), 94-09-C214 (Tumor) and 94-09-C217 (Normal), 94-10-B009 (Tumor) and 94-10B008 (Normal)]. All of the samples, both from tumors and normal tissue, were found to be homozygous for the B type allele. When the nucleotide sequence of the 3' UTR from one tumor sample (BC 102) (SEQ ID NO:6) was determined, it was seen that it differed from the wild type at base 729. The tumor sample contained a C to T base change, which is identical to one of two alterations detected in the breast cancer cell line MCF-7. Additionally, when the 3' UTR sequence from a second tumor sample (4001536-AT) (SEQ ID NO:7) was determined, it also differed from the wild type sequence by a single base. In this sample, base 821 was changed from A to G.

This sequencing data suggests that there are two areas most likely to be mutated. They extend from about nucleotide 200 to about nucleotide 400 and from about nucleotide 600 to about nucleotide 852.

The occurrence of these base changes in the 3' UTR of breast cancer cells classified as belonging to complementation Group B on the basis of their homozygosity for the B type prohibitin allele combined with the genotype and 3' UTR sequence analyses from patients with breast tumors confirm that prohibitin genotype and the 3' UTR sequence can be used at a minimum as a screen for breast cancer susceptibility and as a therapeutic agent for the treatment of cancer.

Additionally, it has been found that only normal cell lines and Group B cell lines (Table 1) could be inhibited from progressing through the cell cycle by the microinjection of the 1.9 kb transcript from the gene. (See, e.g., FIG. 1) It was further determined that only normal cells could be inhibited by the microinjection of the 1.2 kb human transcript.

In four experiments, normal CF-3 cells microinjected with the 1.2 kb human transcript exhibited a 47.8±2.1% inhibition, while HeLa cells from Group B exhibited an insignificant 6.3±1.8% inhibition We also found that fourteen of seventeen cell lines derived from human breast cancers had the same prohibitin genotype as complementation Group B cells. Three breast cancer cell lines with the Group B prohibitin genotype (BT20, SK-BR-3, and MCF-7) were tested and were inhibited from progressing through the cell cycle by the microinjection of the 1.9 kb transcript at a level of 57.7%, 43.6%, and 25.4%, respectively; while one breast cancer cell line (BT549) possessing the genotype of another complementation group was not inhibited. The three breast cancer cell lines expressing the B-type genotype were classified by Olivia Pereira-Smith as belonging to Group B, while the one cell line that was homozygous for the non-B type allele was classified in Group D on the basis of the cells mortalin staining patterns. Wadhwa, et al., *Exp Cell Res* 216:101-106 (1995).

Figure 2:
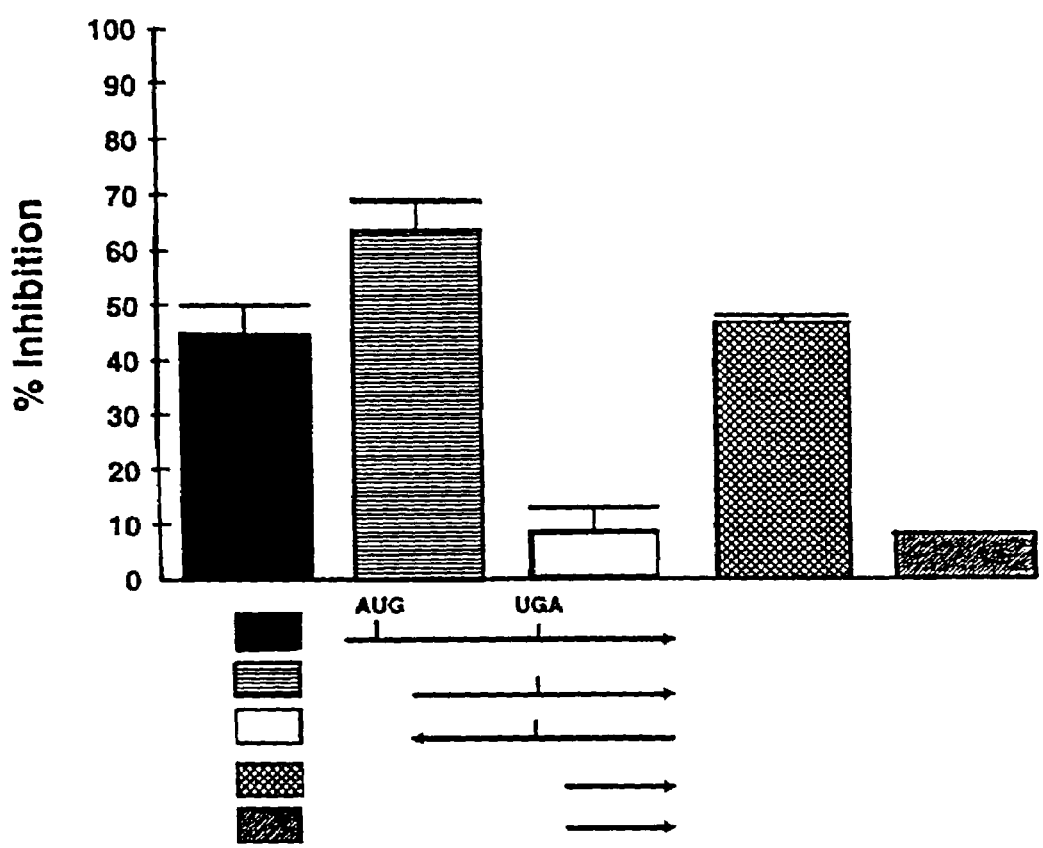
FIG. 2 is a bar graph showing the effect on cell cycle progression by microinjection of truncated prohibitin transcripts into human diploid fobroblasts (CF-3). Schematics of the transcripts are shown below the figure: 1.9 kb full length (solid); truncated sense (horizontal lines); truncated antisense (open); wild-type 852 base 3'UTR (cross-hatched); and mutated 852 base 3'UTR from HeLa (diagonal lines). The values are represented as the mean±the standard error of means of three separate experiments.

The antiproliferative activity of truncated wild-type RNAs and 3'UTR specific wild-type and mutated RNAs was also examined using the microinjection assay in CF-3 cells. (See Example 14) Transcripts were made in both the sense and the antisense orientations from a truncated clone missing approximately 150 bp from the 5' end of the prohibitin mRNA, the 852-base wild-type 3'UTR, and the 852-base mutated HeLa 3'UTR. The sense truncated transcript is missing translational signals as well as the AUG start site and the RNA coding for the first 40 amino acids of prohibitin protein. The sense transcript of this clone was able to strongly inhibit cell cycle progression while the antisense transcript had essentially no effect. The truncated RNA containing only 3'UTR sequence begins approximately 80 bases downstream of the UGA stop codon. The wild-type 3'UTR specific RNA inhibits cell proliferation at a level similar to that seen for the full-length 1.9-kb mRNA and the sense transcript of the longer truncated RNA. The mutated 3'UTR from HeLa, however, has little or no inhibitory activity. Thus, these functional assays show that the wild-type prohibitin 3'UTR alone has a significant inhibitory activity and that mutations in this region eliminate this activity. (See FIG. 2)

These studies indicate that the prohibitin genotype and the 3' UTR sequence should prove useful as a generic cancer susceptibility screen and as a therapeutic agent for a number of types of cancer in addition to its usefulness as a susceptibility screen and therapeutic agent for breast cancer.

TABLE 1

Group B cell lines

| | Designation | Origin |
|---|---|---|
| 1. | HeLa | Cervical carcinoma |
| 2. | GM2096SV9 | Origin-defective SV40-immortalized xeroderma pigmentosum skin fibroblasts |
| 3. | T98G | Glioblastoma |
| 4. | J82 | Bladder carcinoma |

TABLE 2

Normal human fibroblast-like cell lines.

| | Designation | Origin |
|---|---|---|
| 1. | CF-1 | Newborn Foreskin |
| 2. | CF-2 | Newborn Foreskin |
| 3. | HFMD | Newborn Foreskin |
| 4. | AG4525 | Embryonic Skin |
| 5. | IMR90 | Embryonic Lung |
| 6. | IMR91 | Embryonic Lung |
| 7. | JAS | Newborn Foreskin |
| 8. | FeSin | Embryonic Skin |
| 9. | WLW | Adult Foreskin |
| 10. | GM-1 | Adult Skin |
| 11. | GM-2 | Adult Skin |
| 12. | GM970B | Newborn Skin |
| 13. | SW1427 | Embryonic Lung |
| 14. | OS38A | Adult Foreskin |
| 15. | OS40A | Adult Foreskin |
| 16. | OS53A | Adult Foreskin |
| 17. | OSFP | Fetal Skin |
| 18. | CF-3 | Newborn Foreskin |
| 19. | WI-38 | Embryonic Lung |

TABLE 3

DNA samples from normal human tissue

| | Vendor | Number | Origin |
|---|---|---|---|
| 1. | Sigma | D3160-088F3843 | Placenta - Male |
| 2. | Sigma | D6537-089F3860 | Chorionic membrane - Male |
| 3. | Sigma | D3035-088F3844 | Placenta - Female |
| 4. | Sigma | D3035-039F3825 | Placenta - Female |
| 5. | Sigma | D5037-89F3861 | Chorionic membrane - Female |
| 6. | Sigma | D4642-42H6667 | Placenta |
| 7. | Promega | G304-42416 | Blood |
| 8. | Clontech | 6550-1-45641 | Placenta |

TABLE 4

DNA samples from lymphocyte cultures from extended family pedigrees.

| | Designation | Pedigree | Family |
|---|---|---|---|
| 1. | 6995 | K-1329 | 981 |
| 2. | 6997 | K-1329 | 981 |
| 3. | 7042 | K-1329 | 981 |
| 4. | 7014 | K-1329 | 981 |
| 5. | 7018 | K-1329 | 981 |
| 6. | 7036 | K-1329 | 981 |
| 7. | 6981 | K-1329 | 981 |
| 8. | 6980 | K-1329 | 981 |
| 9. | 7047 | K-1329 | 981 |
| 10. | 7433 | K-1329 | 981 |
| 11. | 7085 | K-1329 | 981 |
| 12. | 6990 | K-1331 | 982 |
| 13. | 7057 | K-1331 | 982 |
| 14. | 6987 | K-1333 | 983 |
| 15. | 7038 | K-1333 | 983 |
| 16. | 7348 | K-1345 | 1029 |
| 17. | 7349 | K-1345 | 1029 |

TABLE 5

DNA from blood samples.

|     | Designation | Origin |
| --- | --- | --- |
| 1.  | CF154 | Blood |
| 2.  | CF148-1 | Blood |
| 3.  | CF142-3 | Blood |
| 4.  | CF147 | Blood |
| 5.  | CF140 | Blood |
| 6.  | CF152-1 | Blood |
| 7.  | CF155 | Blood |
| 8.  | CF156-1 | Blood |
| 9.  | CF158 | Blood |
| 10. | CF139 | Blood |
| 11. | CF153 | Blood |
| 12. | CF138 | Blood |
| 13. | CF150-1 | Blood |
| 14. | CF151-1 | Blood |
| 15. | CF143 | Blood |
| 16. | CF137 | Blood |
| 17. | CF145-2 | Blood |
| 18. | CF159 | Blood |
| 19. | CF146-1 | Blood |
| 20. | CF157 | Blood |

TABLE 6

Human breast cancer cell lines.

|     | Designation | Origin |
| --- | --- | --- |
| 1.  | BT-20 | Solid tumor - ductal carcinoma |
| 2.  | BT-474 | Solid tumor - ductal carcinoma |
| 3.  | BT-483 | Solid tumor - ductal carcinoma |
| 4.  | MCF-7 | Pleural effusion - adenocarcinoma |
| 5.  | Hs 578T | Solid tumor - ductal carcinoma |
| 6.  | SK-BR-3 | Pleural effusion - adenocarcinoma |
| 7.  | T-47D | Pleural effusion - ductal carcinoma |
| 8.  | UACC-812 | Solid tumor - ductal carcinoma |
| 9.  | ZR-75-30 | Ascites fluid - ductal carcinoma |
| 10. | ZR-75-1 | Ascites fluid - ductal carcinoma |
| 11. | MDA-MB-330 | Pleural effusion - lobular carcinoma |
| 12. | MDA-MB-361 | Brain metastasis - adenocarcinoma |
| 13. | MDA-MB-415 | Pleural effusion - adenocarcinoma |
| 14. | MDA-MB-453 | Pleural effusion - adenocarcinoma |
| 15. | MDA-MB-435S | Pleural effusion - ductal carcinoma |
| 16. | BT-549 | Lymph node - ductal carcinoma |
| 17. | MDA-MB-436 | Pleural effusion - adenocarcinoma |

TABLE 7

Prohibitin Genotype of Breast Cancer Cell Lines[1]

Homozygous B Type Allele (17)

| | | |
| --- | --- | --- |
| BT-20 | T-47D | MDA-MB-330 |
| BT-474 | UACC-812 | MDA-MB-415 |
| BT-483 | ZR-75-30 | MDA-MB-453 |
| MCF7 | Du 4475 | MDA-MB-468 |
| Hs 578T | MDA-MB-157 | MDA-MB-175 VII |
| SK-BR-3 | MDA-MB-231 | |

Homozygous non-B type Allele (5)

| | | |
| --- | --- | --- |
| BT-549 | MDA-MB-436 | MDA-MB-134 VI |
| UACC-893 | MDA-MB-361 | |

Heterozygous (0)

[1]All cell lines were obtained from the American Type Culture Collection and analyzed by Southern blotting after EcoRI digestion of genomic DNA and/or BsmAI restriction analysis after PCR amplification of a 76 bp segment surrounding the intron 5/exon 6 splice junction.

TABLE 8

Prohibitin 3'UTR Mutations in Three Homozygous B Breast Cancer Cell Lines

| Cell Line | Positions of Base Change | Base Change |
| --- | --- | --- |
| BT-20 | 758 | G to A |
|       | 814 | T to C |
| MCF7  | 236 | G to A |
|       | 729 | C to T |
| SK-BR-3 | 23 | C to T |
|       | 24 | A to G |
|       | 32 | C to T |
|       | 35 | A to C |
|       | 52 | G to A |
|       | 64 | T to C |
|       | 691 | G to T |
|       | 696 | C to A |
|       | 702 | G to T |
|       | 711 | G to A |
|       | 729 | C to T |
|       | 734 | C to A |
|       | 736 | G to A |
|       | 373 | A to T |
|       | 741 | A to C |
|       | 742 | C to T |
|       | 752 | C to T |
|       | 753 | C to T |
|       | 757 | C to T |
|       | 771 | C to T |
|       | 778 | A to C |
|       | 779 | C to A |
|       | 787 | A to G |
|       | 794 | C to T |
|       | 795 | A to G |
|       | 798 | G to T |
|       | 799 | G to T |
|       | 802 | ΔA |
|       | 803 | ΔG |
|       | 804 | ΔG |
|       | 808 | C to T |
|       | 810 | A to G |
|       | 813 | G to C |
|       | 825 | C to T |
|       | 829 | C to T |

The sequence of breast cancer cell lines was compared to wild type sequence from normal human diploid fibroblasts (4, GenBank Acc. #U49725). Two base changes are present in both the BT-20 and MCF7 cells, but 35 base changes (including a 3 base deletion) are detected in the SK-BR-3 cells. Seventy-five percent of the alterations occur in the last 200 bases of the sequence, and 36% of the base changes are C to T transitions.

Example 1—Isolation of Human Prohibitin Gene 3' UTR

The human prohibitin gene 3' UTR was identified and isolated based on the high level of conservation between the rat and human genes. Oligonucleotides designed from the highly conserved exon 7 non-coding region of the rat and human gene were used as a 5' primer (SEQ ID NO:8) along with a 3' primer designed from the published rat sequence (SEQ ID NO:9). The 3' UTR specific fragment was synthesized using the polymerase chain reaction (PCR) (Saiki et al., *Science* 230:1350-1354 (1985)) (incorporated herein by reference) carried out under standard reaction conditions using the manufacturer's recommendations for Stoffel polymerase (Perkin Elmer). Genomic DNA from normal human diploid fibroblasts (IMR-90) isolated by standard methods (Groos-Bellard et al., *Eur J Biochem* 36:32) (incorporated herein by reference) was used as the template for PCR. Following an initial denaturation at 95° C. for 2 minutes, 35 cycles of 95° C., 55° C. and 72° C. for 1 minute each were done in a Perkin Elmer 480 thermal cycler. The reaction products were checked for specificity by analysis on agarose gels stained with ethidium bromide and visualized using ultraviolet light.

The PCR products from the initial wild type and subsequent mutated samples were all cloned into the TA cloning vector pCR-II™ (Invitrogen Corp., San Diego, Calif.) following the manufacturer's instructions and recombinant clones were recovered using standard antibiotic selection protocols supplied with the pCR-II™ (Invitrogen Corp., San Diego, Calif.) cloning kit. These plasmids also have the M13 forward and reverse primer sites for convenient sequencing of clones.

Candidate human prohibitin cDNA clones containing the full length 3' UTR portion of the transcript were also isolated from a cDNA library screen using an oligonucleotide probe (SEQ ID NO:9). Suggs et al., *Proc Natl Acad Sci* 78:6613 (1981), incorporated herein by reference. Positive clones isolated from the screen were characterized by restriction mapping. Human clones from the genomic PCR product and cDNAs representing transcripts containing the entire 3' UTR were sequenced using the ABI Taq cycle sequencing protocol (Perkin Elmer, Norwalk, Conn.). Sequences were aligned using the University of Wisconsin GCG packages. The cDNA and genomic sequences were identical, thus showing that the full 3' UTR (SEQ ID NO: 10) is transcribed from the genome without introns.

Example 2—Isolation of 1.2 and 1.9 kb Prohibitin Transcripts

The two human prohibitin transcripts were initially detected and their expression levels characterized by Northern analysis. Liu et al., *Biochem Biophy Res Comm* 201: 409-414 (1944), incorporated herein by reference; Jupe et al., *Exp Cell Res* 218:577-580 (1995), incorporated herein by reference. The cloning and isolation of the cDNA's from the 1.9 kb transcripts is described above in Example 1. In the process of these screenings, clones of the 1.2 kb transcript that match the previously described human clone were independently obtained. Sato et al., *Cancer Res* 52:1643-1646 (1992).

Example 3—Preparation of Human Prohibitin cDNA

The human prohibitin cDNAs were isolated and characterized as described in Example 1 above. All plasmid clones described in this application were purified using a standard boiling lysis preparation (Holmes and Quigley, *Anal Biochem* 114:193-197 (1981), incorporated herein by reference) or the alkaline lysis method combined with anion exchange column purification using Quiagen Tips. (Quiagen, Incorporated, Chatsworth, Calif.).

Example 4—PCR Amplification of the 3' UTR

The PCR conditions for amplification of the 3' UTR are described in Example 1. The primer set that was successfully used to clone this 852 bp region from all of the wild type and mutated samples are as follows:
sense primer: 5'-CCCCAGAAATCACTGTG-3' (SEQ ID NO:8)
antisense primer: 5'-GGAAGGTCTGGGTGTCATTT-3' (SEQ ID NO:9)

Example 5—Sequencing

All sequencing reactions were done using automated sequencing by the ABI methods (see Example 1 above).

Example 6—PCR Amplification of Exon 6

The PCR reactions were performed under the same temperature and cycling conditions outlined in Example 1. The primers used to produce a 191 bp fragment were as follows:
sense primer: 5'-CAATCACACTGCCTCATC-3[1] (SEQ ID NO:11)
antisense primer: 5'-TGAGTGCCGGAGAAAGGG-3' (SEQ ID NO:12)
The primers used to produce a 76 bp fragment were as follows:
sense primer: 5'-CAATCACACTGCCTCATC-3' (SEQ ID NO:11)
antisense primer: 5'-CCGCTTCTGTGAACTCC-3' (SEQ ID NO: 13)

Example 7—Cloning and Sequencing of Exon 6

The products of exon 6 PCR reactions were cloned into the TA cloning vector described in Example 1 above. The sequencing of these cloned products as well as direct sequencing of exon 6 PCR products have been performed as described in Example 5 above.

Example 8—RFLP Assay of Exon 6

The sequence polymorphism identified in exon 6 leads to differential cleavage by the restriction enzyme BsmAI available from New England Biolabs (Beverly, Mass.). The B type allele is not cleaved by the enzyme while the non-B type allele is. These digests were performed on the PCR products described in Example 6 according to the manufacturer's instructions and analyzed using agarose gel electrophoresis on 4% NuSieve gels as described in Example 1.

Example 9—SSCP Analysis of Exon 6

Single strand conformation polymorphism (SSCP) screening was originally used to detect exon 6 polymorphisms in prohibitin. Jupe et al., *Exp Cell Res* 218:577-580 (1995), incorporated herein by reference. The method used was a cold SSCP protocol. Hongyo et al., *Nuc Acids Res* 21:3637-3642 (1993), incorporated herein by reference. PCR products were synthesized and checked as described above, and only those displaying a single predicted band were chosen for SSCP analysis. The DNA products for SSCP analysis were then subjected to denaturation in formamide solution at 95° C. and rapidly cooled on ice. The samples were then separated on 10 or 20% polyacrylamide gels, stained with ethidium bromide and visualized with UV light.

Example 10—Isolation and Sequencing of DNA from Additional 3' UTR Samples

The methods used in the identification, cloning, isolation and sequencing of all additional 3' UTR sequences were as described in Example 1 above.

Example 11—Reintroduction of Wild Type 3' UTR

The human full length transcripts or portions containing only the 3' UTR are maintained in the pCRII™ vector described above. These sequences are available for transfer into appropriate mammalian vectors for gene transfer. The current technology for human gene therapy is rapidly emerging and appropriate vectors for these applications are being developed. See, e.g., Deisseroth et al., *Proc Am Assoc Can Res* 36:655-656 (1995), incorporated herein by reference.

Example 12—SSCP Analysis of Prohibitin Gene

The method used for the SSCP analysis of the prohibitin gene were as described in Example 9 above. The SSCP analysis of the remaining exons (Nos. 2-5 and 7) was carried out using the same methods and appropriate primer sets for each exon as follows:

| Exon | Sense Primer | Antisense Primer |
| --- | --- | --- |
| 2 | TGGAGGGACAGTGGGT (SEQ ID NO: 14) | TCTAACTAGCTGCAAA (SEQ ID NO: 15) |
| 3 | AGAGGATTTTTATGACATGTC (SEQ ID NO: 16) | GAGCACCTCTTCCACACTCCC (SEQ ID NO: 17) |
| 4 | GTGCTCTGGGCTCGAGC (SEQ ID NO: 18) | CTAAAGGCCCCTGTTCACTCA (SEQ ID NO: 19) |
| 5 | CCTCATTAACCTGACCTGCCC (SEQ ID NO: 20) | TAAACGAGAACTGCAGCCCCT (SEQ ID NO: 21) |
| 7 | GCCTTTGGTTGTAGCCTG (SEQ ID NO: 22) | CACAGTGATTTCTGGGG (SEQ ID NO: 23) |

Example 13—SSCP Analysis of 3' UTR

An SSCP analysis of the 3' UTR or regions thereof can be performed as described in Example 9 above. Choice and construction of the appropriate primers for the PCR amplification of the 3' UTR or a portion thereof are well within the skill of one of ordinary skill in the art given the sequence of the 3' UTR provided herein.

Example 14—Microinjection Assay

The antiproliferative activity of prohibitin was assayed following the microinjection of various in vitro produced RNA transcripts. Nuell, M. J., et al., *Mol. Cell. Biol.* 11:1372-1381 (1991). Briefly, cells were synchronized in early G1 with lovastatin (provided by A. W. Alberts of Merck, Sharp and Dohme Research Pharmaceuticls, Rahway, N.J.) by the method of Keyomarsi et al. Keyomarsi, K., et al., *Cancer Res.* 51:3602-3609 (1991). Synchronized cells (200-300 per experiment) from all of the lines described above were microinjected with in vitro produced transcript at a concentration of 1 mg/ml using an Eppendorf Model 5242 microinjector. The full-length 1.9-kilobase (kb) cDNA and several truncated cDNAs cloned into either pBSIISK+ (Stratagene, La Jolla, Calif.) or pCRII (Invitrogen, San Diego, Calif.) were used to synthesize in vitro transcripts using the mMESSAGE mMACHINE (Ambion, Inc., Austin, Tex.). Truncated transcripts syntehsized in both the sense and antisense orientation from a clone missing approximately 150 bp of the 5' end of the cDNA were utilized. The sense transcript was missing translational signals as well as the AUG start site and the region coding for the first 40 amino acids of the prohibitin protein. Transcripts containing only 3'UTR sequences were also tested in this assay. These 850 base transcripts begin approximately 80 bases downstream from the UGA stop codon and were generated from a 3'UTR clone with wild-type sequence and a clone with mutated sequence (HeLa). Microinjected cells were stimulated to move through the cell cycle in the presence of [$^3$H]thymadine, and inhibitory activity was calculated following autoradiography. Nuell, M. J., et al., *Mol. Cell. Biol.* 11:1372-1381 (1991).

We claim:

1. A purified polynucleotide comprising a portion of the 3' untranslated region of the prohibitin gene, the portion comprising a nucleotide sequence beginning at nucleotide 4 of SEQ ID NO:10 and ending at least at nucleotide 161 of SEQ ID NO:10, wherein said polynucleotide lacks prohibitin coding regions.

2. The polynucleotide of claim 1, wherein the portion of the 3' untranslated region of the prohibitin gene comprises a nucleotide sequence beginning at nucleotide 4 of SEQ ID NO:10 and ending *at nucleotide* 942 of SEQ ID NO:10.

3. The polynucleotide of claim 1, wherein the portion of the 3' untranslated region of the prohibitin gene comprises a nucleotide sequence beginning at nucleotide 158 of SEQ ID NO:10 and ending at nucleotide 942 of SEQ ID NO:10.

4. The polynucleotide of claim 3, wherein the portion of the 3' untranslated region of the prohibitin gene comprises a nucleotide sequence beginning nucleotide 89 of SEQ ID NO:10 and ends at nucleotide 942 of SEQ ID NO:10.

5. A polynucleotide comprising a sequence selected from the group consisting of SEQ ID NO:2, NO:3, NO:4, NO:5, NO:6 and NO:7.

6. The polynucleotide of claim 5, wherein the polynucleotide comprises SEQ ID NO:2.

7. The polynucleotide of claim 5, wherein the polynucleotide comprises SEQ ID NO:4.

8. The polynucleotide of claim 5, wherein the polynucleotide comprises SEQ ID NO:5.

9. The polynucleotide of claim 5, wherein the polynucleotide comprises SEQ ID NO:6.

10. The polynucleotide of claim 5, wherein the polynucleotide comprises SEQ ID NO:7.

11. The polynucleotide of claim 5, wherein the polynucleotide comprises SEQ ID NO:3.

* * * * *